(12) United States Patent
Tang et al.

(10) Patent No.: US 10,478,378 B2
(45) Date of Patent: Nov. 19, 2019

(54) MULTI-FUNCTIONAL ELECTRO-SPOON NEEDLE THERAPEUTIC APPARATUS

(71) Applicants: Qiang Tang, Harbin (CN); Luwen Zhu, Harbin (CN); Zhejiang Scobry Medical Technology Co., Ltd., Shaoxing (CN)

(72) Inventors: Qiang Tang, Harbin (CN); Luwen Zhu, Harbin (CN); Yan Wang, Harbin (CN); Yanli Xing, Harbin (CN); Zhishun Yu, Harbin (CN)

(73) Assignees: Qiang Tang, Harbin, Heilongjiang (CN); Luwen Zhu, Harbin, Heilongjiang (CN); ZHEJIANG SCOBRY MEDICAL TECHNOLOGY CO., LTD, Shaoxing, Zhejiang (CN)

( * ) Notice: Subject to any disclaimer, the term of this patent is extended or adjusted under 35 U.S.C. 154(b) by 99 days.

(21) Appl. No.: 15/557,133

(22) PCT Filed: Mar. 9, 2016

(86) PCT No.: PCT/CN2016/075910
§ 371 (c)(1),
(2) Date: Sep. 11, 2017

(87) PCT Pub. No.: WO2016/146002
PCT Pub. Date: Sep. 22, 2016

(65) Prior Publication Data
US 2018/0042815 A1   Feb. 15, 2018

(30) Foreign Application Priority Data

Mar. 16, 2015   (CN) .......................... 2015 1 0112368

(51) Int. Cl.
*A61N 1/04*   (2006.01)
*A61H 39/04*   (2006.01)
(Continued)

(52) U.S. Cl.
CPC ............. *A61H 39/04* (2013.01); *A61H 7/006* (2013.01); *A61H 39/002* (2013.01);
(Continued)

(58) Field of Classification Search
CPC .......................... A61H 2205/02; A61H 39/002
See application file for complete search history.

(56) References Cited

U.S. PATENT DOCUMENTS 9,061,148 B2 *   6/2015   Bachinski .......... A61N 1/36014

\* cited by examiner

*Primary Examiner* — Michael J D Abreu
(74) *Attorney, Agent, or Firm* — Leong C. Lei (57) ABSTRACT

Disclosed is a multi-functional electro-spoon needle therapeutic apparatus, which includes a top cover, locating pieces, a fixed lid, a rear cover, electro-spoon needles and an adjustment mechanism, wherein the locating pieces are respectively mounted on the top cover and the rear cover, and each locating piece is provided with a long groove; the fixed lid is respectively fixed on the top cover and the rear cover so as to respectively hold the locating pieces between the top cover and the fixed lid and between the rear cover and the fixed lid; the rear cover is arranged behind the top cover and connected to the top cover via the adjustment mechanism; and the electro-spoon needles are mounted in the long grooves of the locating pieces and can move along the long grooves. The apparatus has a simple structure, so a patient can perform acupuncture by himself.

8 Claims, 7 Drawing Sheets

(51) Int. Cl.
  *A61N 1/36*   (2006.01)
  *A61H 39/00*  (2006.01)
  *A61H 39/08*  (2006.01)
  *A61H 7/00*   (2006.01)

(52) U.S. Cl.
  CPC ......... *A61H 39/083* (2013.01); *A61H 39/086* (2013.01); *A61N 1/0484* (2013.01); *A61N 1/36* (2013.01); *A61N 1/36017* (2013.01); A61H 2201/0107 (2013.01); A61H 2201/0192 (2013.01); A61H 2201/1604 (2013.01); A61H 2205/021 (2013.01)

FIG. 7 ered nuovaMULTI-FUNCTIONAL ELECTRO-SPOON NEEDLE THERAPEUTIC APPARATUS

BACKGROUND OF THE INVENTION

1. Field of the Invention

The present invention relates to an acupuncture appliance, and more particularly to a multi-functional electro-spoon needle therapeutic apparatus which belongs to the technical field of medical devices.

2. Description of the Prior Art

The acupuncture therapy is a method of treating diseases, with a needle to press the surface of an acupuncture point. A spoon needle is one of the ancient nine needles, about 3 to 4 inches, which is made of a thick steel wire (it may be made of a hardwood or bone material). The needle head is blunt as millet, so it won't pierce the skin. The needle is used to press the surface of an acupuncture point for promoting blood circulation or alleviating pain. It is clinically used for treating some painful diseases, such as stomachache, abdominal pain, indigestion, neurological vomiting, pregnancy vomiting, neurosis, and the like. When in use, the needle is pressed against the surface of an acupuncture point to get the energy of the meridian. As to the deficiency syndrome tonifying method, the needle is gently pressed against an acupuncture point until the local skin flushes and the pain is alleviated. After the needle is removed, the acupuncture point is slightly kneaded with the hands. As to the excessive syndrome reducing method, the needle is heavily pressed against the acupuncture point until the patient feels soreness to spread up and down, and then the needle is removed. In recent years, ancient needles are combined with modern science and technology to form electro-spoon needles or acoustic electro-spoon needles, used to activate meridian sensation.

However, the existing acupuncture and moxibustion therapy is usually carried out by specialized acupuncturists. Acupuncturists need to first identify the acupuncture points. The operation is professional, so a general patient is unable to operate the needle by himself. Patients must go to the hospital for acupuncture therapy. The number of patients for the hospital acupuncturist to treat diseases is limited.

Accordingly, the inventor of the present invention has devoted himself based on his many years of practical experiences to solve these problems.

SUMMARY OF THE INVENTION

In order to solve the above-mentioned technical problems, the primary object of the present invention is to provide a multi-functional electro-spoon needle therapeutic apparatus which is simple in structure and convenient in adjustment and can be operated by a patient.

In order to achieve the aforesaid object, the multi-functional electro-spoon needle therapeutic apparatus of the present invention comprises a top cover, a plurality of locating pieces, two fixed lids, a rear cover, a plurality of electro-spoon needles, and an adjustment mechanism. The plurality of locating pieces are mounted on the top cover and the rear cover, respectively. Each of the locating pieces is provided with a long groove. The two fixed lids are fixed on the top cover and the rear cover, respectively. The locating pieces are respectively held between the top cover and one of the fixed lids and between the rear cover and the other of the fixed lids. The rear cover is arranged behind the top cover and connected to the top cover through the adjustment mechanism. The electro-spoon needles are mounted in the long grooves of the locating pieces and movable along the long grooves, respectively.

Preferably, each of the electro-spoon needles includes a needle bar, an electrode member, a hollow screw, a locking nut, a silicone plug, and a cap. The electrode member is held at a bottom of the hollow screw and is in contact with the needle bar. The locking nut is screwed to the hollow screw. The silicone plug is a flexible silicone plug accommodated in the hollow screw. The silicone plug elastically holds the needle bar. The needle bar is vertically inserted through the locking nut, the silicone plug, the hollow screw and the electrode member. A cap is disposed on a top of the needle bar.

Preferably, each of the positioning pieces is sandwiched between the hollow screw and the locking nut. The needle bar is inserted through the long groove.

Preferably, a bottom of each of the positioning pieces is provided with a wiring groove. A bus slot is provided at one side of the rear cover.

Preferably, the electrode member includes a base, a tab, and a plurality of resilient arms. The base is mounted to the bottom of the hollow screw. The tab is located at one side of the base and is inserted into the wiring groove. The resilient arms are disposed under the base and resiliently lean against the needle bar.

Preferably, the adjustment mechanism includes a rack, a rear cover mounting plate, a knob seat, a knob, and a gear. The rack is held on the top cover. The rear cover mounting plate is fixedly connected to the rear cover. The knob seat is mated with the rear cover mounting plate. The knob is pivotally connected to the knob seat. The gear is connected to the knob and linked by the knob. The gear is engaged with the rack.

Preferably, a rubber gasket is provided between the knob seat and the knob.

Preferably, the adjustment mechanism is disposed on the top cover close to two sides of the rear cover.

Preferably, each of the positioning pieces is provided with at least two of the electro-spoon needles.

Compared with the prior art, the present invention has the following beneficial effects:

1. The multi-functional electro-spoon needle therapeutic apparatus of the present invention is simple in structure. The electro-spoon needles can be adjusted according to the acupuncture points of the user's head. After the apparatus is debugged by a professional, a patient can perform acupuncture by himself at home, and the apparatus is convenient to use.

2. The space between the top cover and the rear cover of the multi-functional electro-spoon needle therapeutic apparatus of the present invention is adjustable, so the apparatus is suitable for different users.

3. The wiring of the multi-functional electro-spoon needle therapeutic apparatus of the present invention is arranged in the wiring groove, so that the wiring is simple and the appearance of the product is pleasing to the eyes.

DETAILED DESCRIPTION OF THE PREFERRED EMBODIMENTS

Embodiments of the present invention will now be described, by way of example only, with reference to the accompanying drawings.

As shown in FIG. 1 to FIG. 7, the present invention discloses a multi-functional electro-spoon needle therapeutic apparatus. The multi-functional electro-spoon needle therapeutic apparatus comprises a top cover 1, a plurality of locating pieces 2, two fixed lids 3, a rear cover 4, a plurality of electro-spoon needles 5, and an adjustment mechanism 6.

Figure 1:
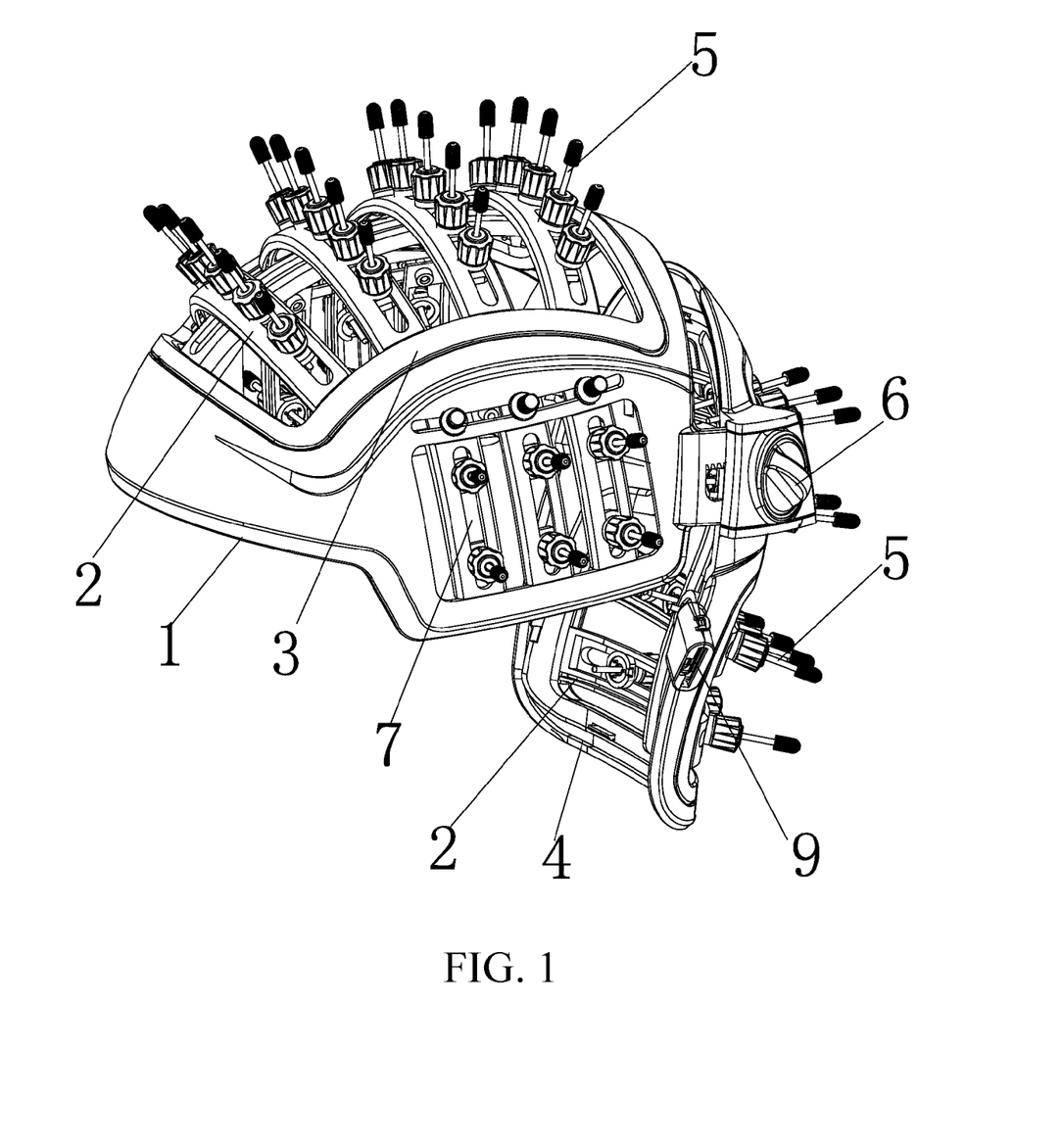
FIG. 1 is a perspective view of the multi-functional electro-spoon needle therapeutic apparatus of the present invention.
Figure 2:
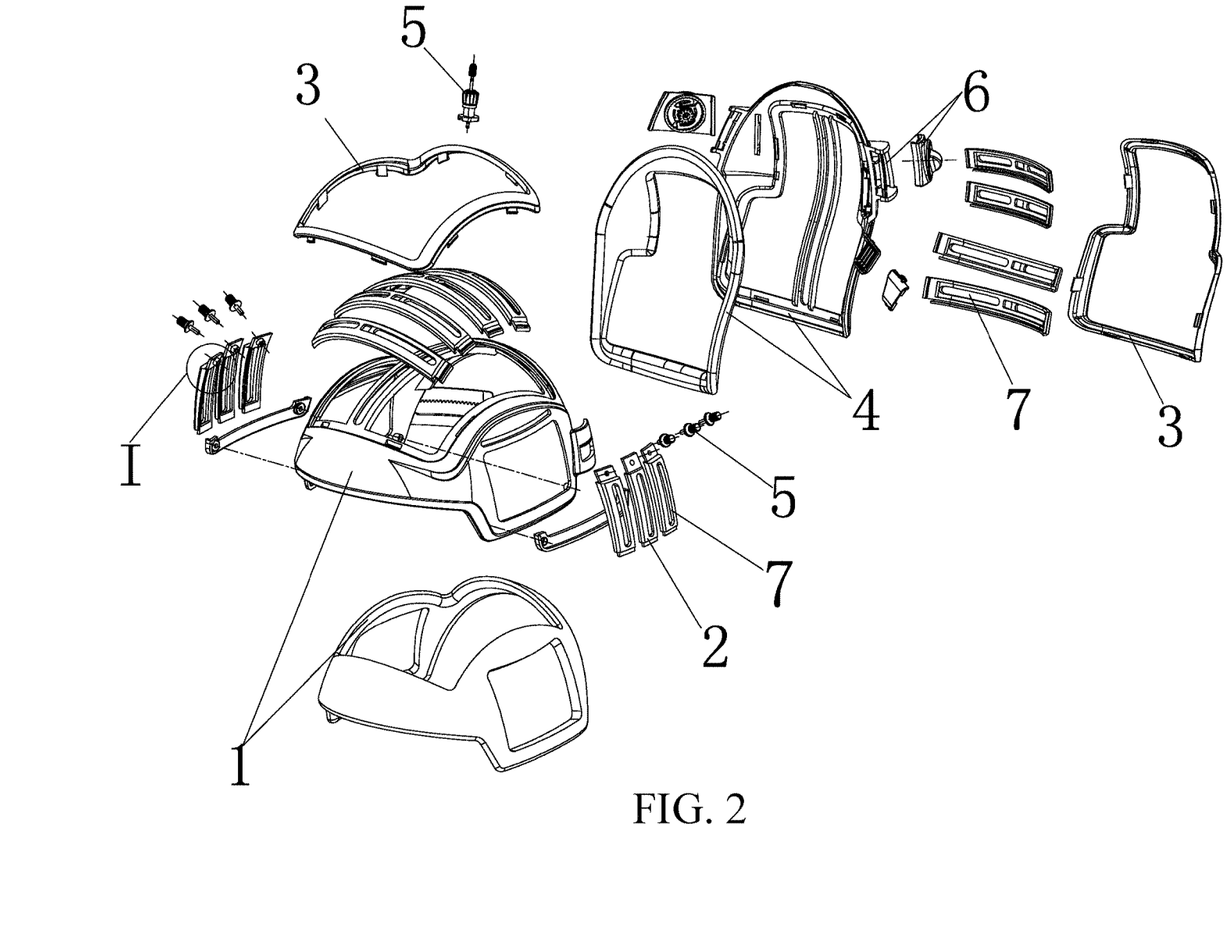
FIG. 2 is an exploded view of the multi-functional electro-spoon needle therapeutic apparatus of the present invention.

The plurality of locating pieces 2 are mounted on the top cover 1 and the rear cover 4, respectively. Each locating piece 2 is provided with a long groove 7. The bottom of the positioning piece 2 is provided with a wiring groove 8.

The two fixed lids 3 are fixed on the top cover 1 and the rear cover 4, respectively. The locating pieces 2 are respectively held between the top cover 1 and the fixed lid 3 and between the rear cover 4 and the fixed lid 3.

The rear cover 4 is arranged behind the top cover 1 and connected to the top cover 1 via the adjustment mechanism 6. The adjustment mechanism 6 is disposed on the top cover 1 close to both sides of the rear cover 4. A bus slot 9 is provided at one side of the rear cover 4 so as to facilitate the energization of wires.

The electro-spoon needles 5 are mounted in the long grooves 7 of the locating pieces 2 and can be adjusted along the long grooves 7 according to the acupuncture points of the user's head. Each of the positioning pieces 2 is provided with at least two electro-spoon needles 5. The electro-spoon needles are connected with the wires (not shown) so that the electro-spoon needles 5 are energized to generate a pulse signal to stimulate the corresponding acupuncture points. The working principle is the prior art and will not be described hereinafter.

Figure 3:
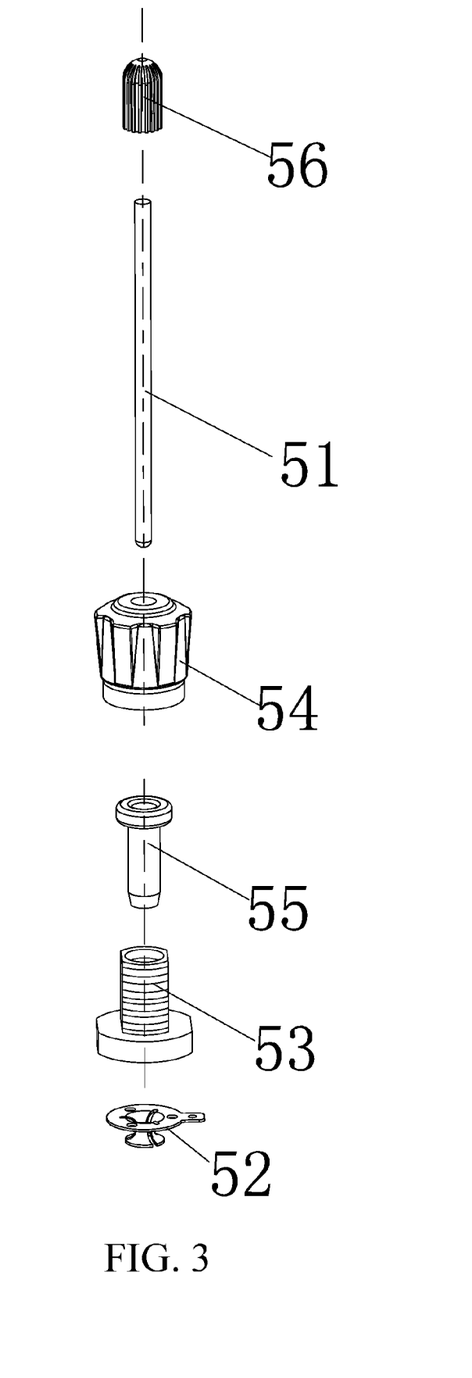
FIG. 3 is an exploded view of the electro-spoon needle in FIG. 1.
Figure 4:
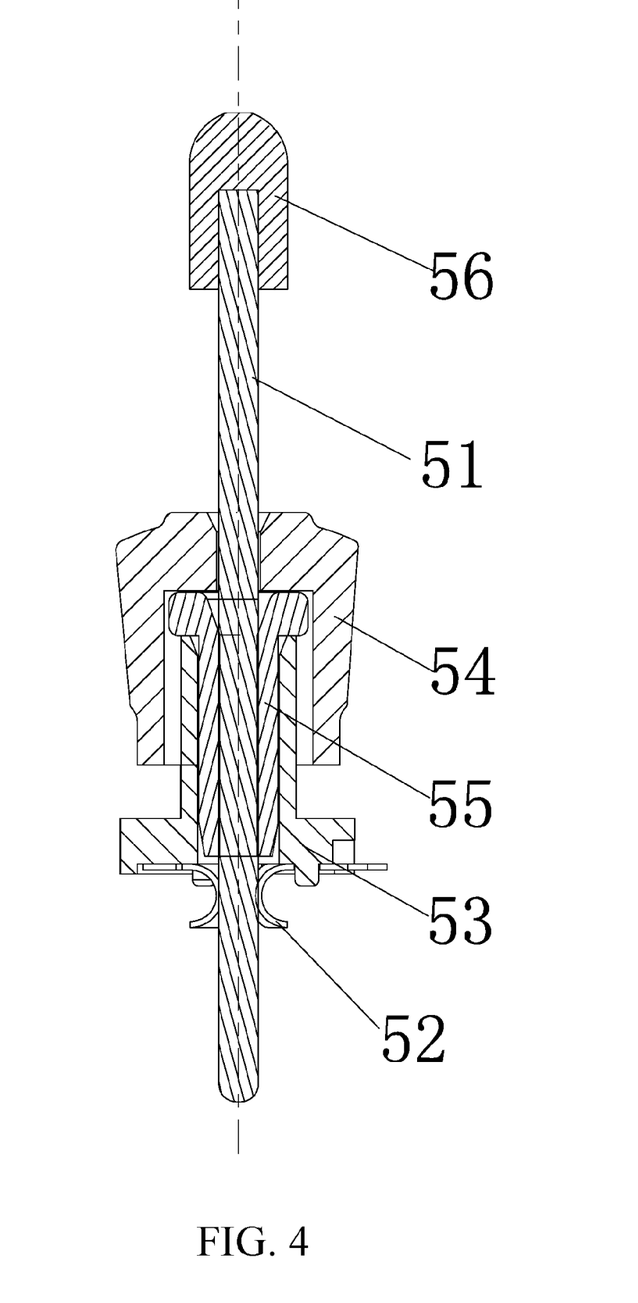
FIG. 4 is a sectional view of the electro-spoon needle in FIG. 1.

Furthermore, the electro-spoon needle 5 includes a needle bar 51, an electrode member 52, a hollow screw 53, a locking nut 54, a silicone plug 55, and a cap 56.

Figure 7:
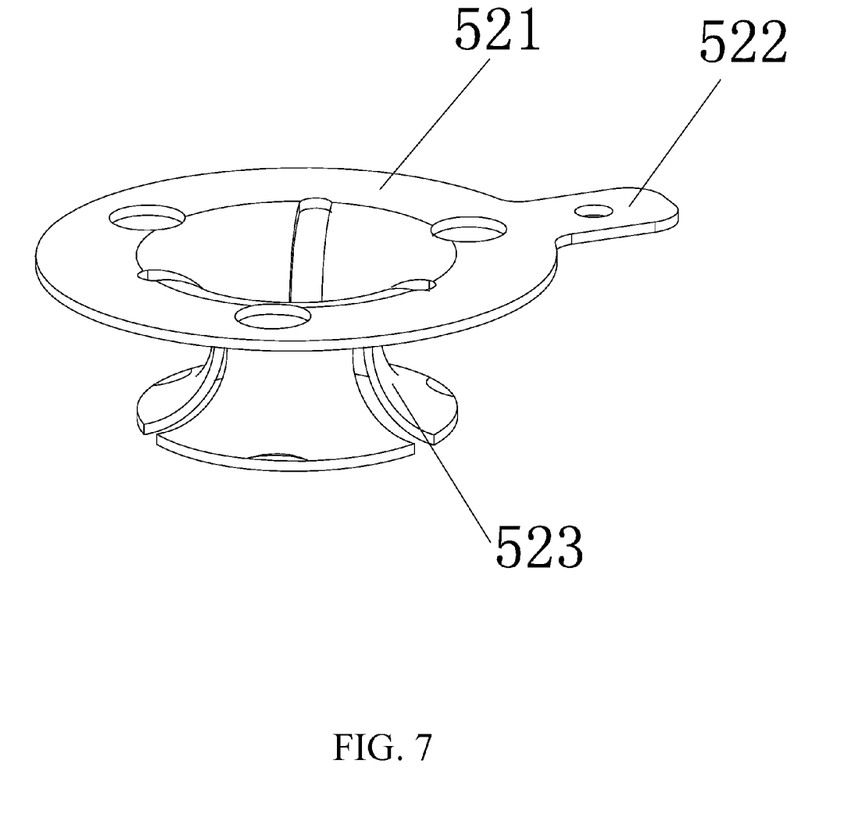
FIG. 7 is an enlarged view of the electrode member in FIG. 3.

The electrode member 52 is held at the bottom of the hollow screw 53 and is in contact with the needle bar 51. Specifically, the electrode member 52 includes a base 521, a tab 522, and a plurality of resilient arms 523, as shown in FIG. 7. Wherein, the base 521 is mounted to the bottom of the hollow screw 53. The tab 522 is located at one side of the base 521 and inserted into the wiring groove 8. The wire is disposed in the wiring groove 8 and connected with the tab 522 so that the overall wiring is not exposed. The appearance is pleasing to the eyes. The resilient arms 523 are disposed under the base 521 and resiliently lean against the needle bar 51 so that the needle bar 51 is pulsed.

The silicone plug 55 is a flexible silicone plug accommodated in the hollow screw 53, which elastically holds the needle bar 51.

The needle bar 51 is vertically inserted through the locking nut 54, the silicone plug 55, the hollow screw 53 and the electrode member 52 to pass through the long groove 7. The bottom of the needle bar 51 is configured to get contact with the user's skin. The cap 56 is disposed on the top of the needle bar 51. When it is necessary to adjust the vertical length of the needle bar 51, the needle bar 51 is pulled up or pressed down. The needle bar 51 can be positioned by the elasticity of the silicone plug 55 when the length is adjusted to a desired position.

Furthermore, the locking nut 54 is screwed to the hollow screw 53. The positioning piece 2 is sandwiched between the hollow screw 53 and the locking nut 54. When the position of the electro-spoon needle 5 in the long groove 7 needs to be adjusted, the locking nut 54 is unscrewed so that the electro-spoon needle 5 can be moved in the long groove 7. After the needle bar 51 is aligned with the corresponding acupuncture point, the locking nut 54 is tightened to position the electro-spoon needle 5 in place.

Figure 5:
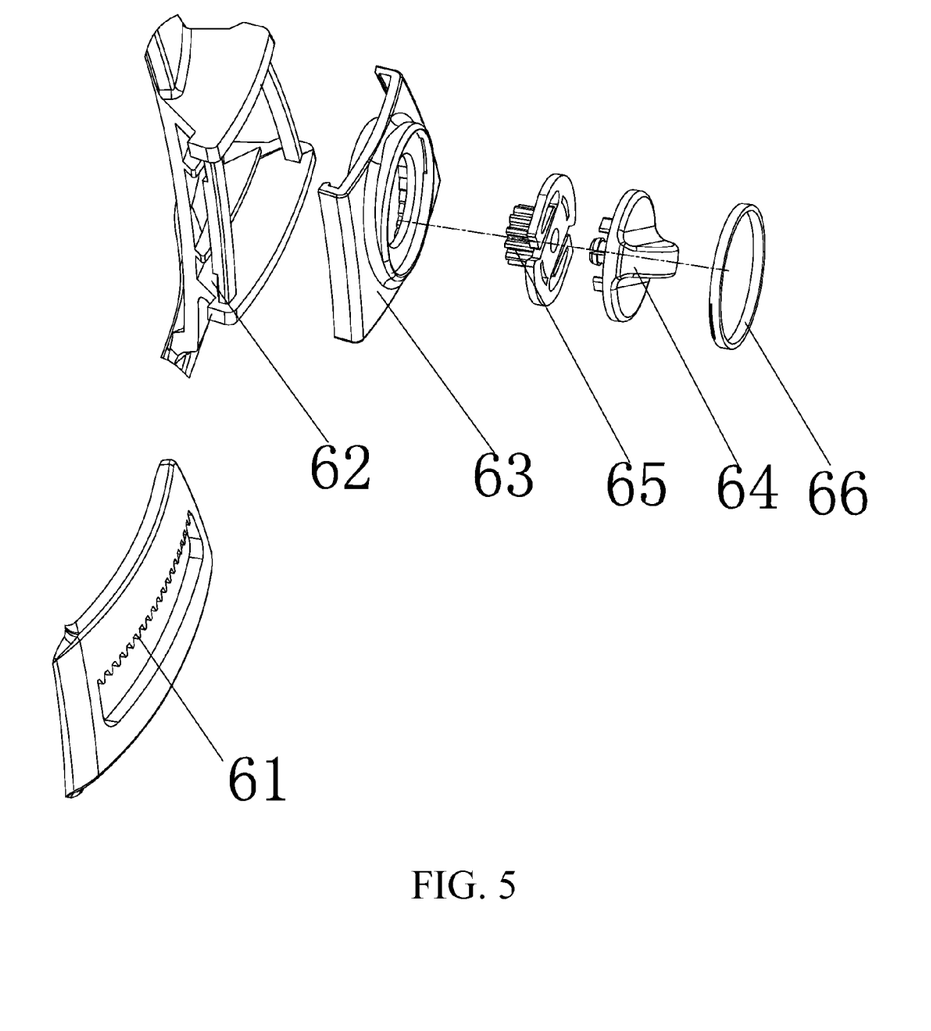
FIG. 5 is an exploded view of the adjustment mechanism in FIG. 1.
Figure 6:
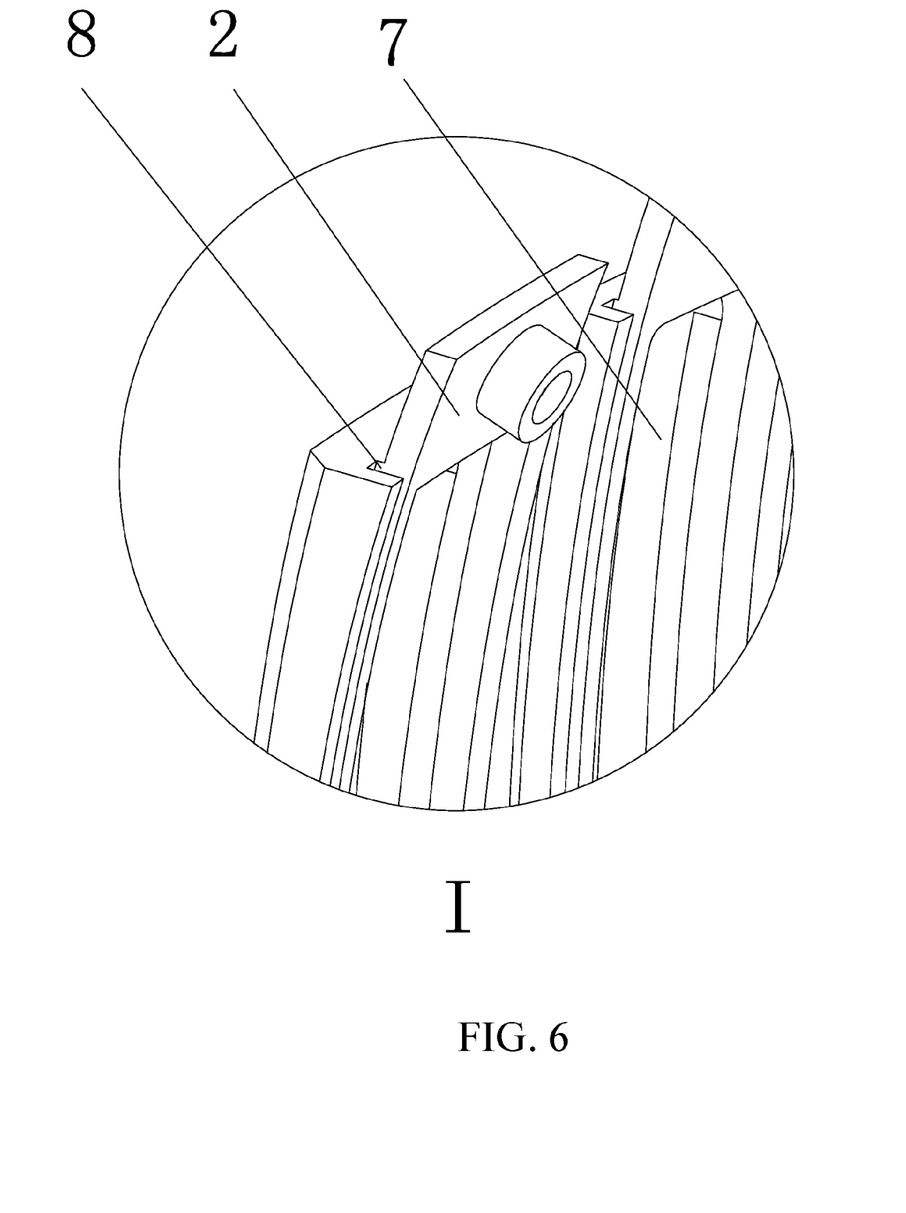
FIG. 6 is an enlarged view of circle I in FIG. 1.

The adjustment mechanism 6 includes a rack 61, a rear cover mounting plate 62, a knob seat 63, a knob 64, and a gear 65. Wherein, the rack 61 is held on the top cover 1. The rear cover mounting plate 62 is fixedly connected to the rear cover 4. The knob seat 63 is mated with the rear cover mounting plate 62. The knob 64 is pivotally connected to the knob seat 63. The gear 65 is connected to the knob 64 and linked by the knob 64. The gear 65 is engaged with the rack 61. A rubber gasket 66 is provided between the knob seat 63 and the knob 64.

The operation of the adjustment mechanism 6 is described below. When it is necessary to adjust the relative position between the top cover 1 and the rear cover 4, the knob 64 is turned to drive the gear 65. The gear 65 is moved along the rack 61, such that the rear cover 4 is moved relative to the top cover 1.

When in use, the multi-functional electro-spoon needle therapeutic apparatus of the present invention is worn on the patient's head, and the relative position between the top cover 1 and the rear cover 4 is adjustable through the adjustment mechanism 6. The locking nut 54 of the electro-spoon needle 5 is loosened. After the electro-spoon needle 5 is aligned with the corresponding acupuncture point of the user, the locking nut 54 is tightened. The needle bar 51 is rotated by the cap 56 for the needle bar 51 to press the corresponding acupuncture point 56. When all the electro-spoon needles 5 are adjusted in place, the needles are electrified for acupuncture therapy. The electro-spoon needles 5 of the multi-functional electro-spoon needle therapeutic apparatus of the present invention can be adjusted according to the acupuncture points of the user's head. After the apparatus is debugged by a professional, a patient can perform acupuncture by himself at home, and the apparatus is convenient to use.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A multi-functional electro-spoon needle therapeutic apparatus, comprising a top cover, a plurality of locating pieces, two fixed lids, a rear cover, a plurality of electro-spoon needles, and an adjustment mechanism; the plurality of locating pieces being mounted on the top cover and the rear cover respectively, each of the locating pieces being provided with a long groove; the two fixed lids being fixed on the top cover and the rear cover respectively, the locating pieces being respectively held between the top cover and one of the fixed lids and between the rear cover and the other of the fixed lids; the rear cover being arranged behind the top cover and connected to the top cover through the adjustment mechanism; the electro-spoon needles being mounted in the long grooves of the locating pieces and movable along the long grooves respectively; wherein each of the electro-spoon needles includes a needle bar, an electrode member, a hollow screw, a locking nut, a silicone plug, and a cap; the electrode member is held at a bottom of the hollow screw and is in contact with the needle bar; the locking nut is screwed to the hollow screw; the silicone plug is a flexible silicone plug accommodated in the hollow screw, the silicone plug elastically holds the needle bar; the needle bar is vertically inserted through the locking nut, the silicone plug, the hollow screw and the electrode member; and the cap is disposed on a top of the needle bar.

2. The multi-functional electro-spoon needle therapeutic apparatus as claimed in claim 1, wherein each of the positioning pieces is sandwiched between the hollow screw and the locking nut; and the needle bar is inserted through the long groove.

3. The multi-functional electro-spoon needle therapeutic apparatus as claimed in claim 2, wherein a bottom of each of the positioning pieces is provided with a wiring groove; and a bus slot is provided at one side of the rear cover.

4. The multi-functional electro-spoon needle therapeutic apparatus as claimed in claim 3, wherein the electrode member includes a base, a tab, and a plurality of resilient arms; the base is mounted to the bottom of the hollow screw; the tab is located at one side of the base and is inserted into the wiring groove; the resilient arms are disposed under the base and resiliently lean against the needle bar.

5. The multi-functional electro-spoon needle therapeutic apparatus as claimed in claim 1, wherein the adjustment mechanism includes a rack, a rear cover mounting plate, a knob seat, a knob, and a gear; the rack is held on the top cover; the rear cover mounting plate is fixedly connected to the rear cover; the knob seat is mated with the rear cover mounting plate; the knob is pivotally connected to the knob seat; the gear is connected to the knob and linked by the knob; and the gear is engaged with the rack.

6. The multi-functional electro-spoon needle therapeutic apparatus as claimed in claim 5, wherein a rubber gasket is provided between the knob seat and the knob.

7. The multi-functional electro-spoon needle therapeutic apparatus as claimed in claim 6, wherein the adjustment mechanism is disposed on the top cover close to two sides of the rear cover.

8. The multi-functional electro-spoon needle therapeutic apparatus as claimed in claim 1, wherein each of the positioning pieces is provided with at least two of the electro-spoon needles.

* * * * *